United States Patent
Crosby et al.

(10) Patent No.: US 9,987,185 B1
(45) Date of Patent: Jun. 5, 2018

(54) TRANSDUCER DEVICES, APPARATUS, SYSTEMS AND METHODS OF OPERATION

(71) Applicant: CAMS Medical Instruments, Inc., Orlando, FL (US)

(72) Inventors: Charles J. Crosby, Orlando, FL (US); Nelson Conrad Dove, Hazel Green, AL (US)

(73) Assignee: CAMS Medical Instruments, Inc., Orlando, FL (US)

( * ) Notice: Subject to any disclaimer, the term of this patent is extended or adjusted under 35 U.S.C. 154(b) by 290 days.

(21) Appl. No.: 14/568,913

(22) Filed: Dec. 12, 2014

Related U.S. Application Data

(63) Continuation-in-part of application No. 13/952,091, filed on Jul. 26, 2013, now Pat. No. 9,463,332, which is a continuation-in-part of application No. 11/859,413, filed on Sep. 21, 2007, now abandoned, which is a continuation-in-part of application No. 11/441,483, filed on May 26, 2006, now Pat. No. 7,883,534, which is a continuation-in-part of application No. 10/084,008, filed on Feb. 27, 2002, now Pat. No. 7,077,857.

(Continued)

(51) Int. Cl.
*A61N 5/00* (2006.01)
*A61H 1/00* (2006.01)
*A61N 5/06* (2006.01)

(52) U.S. Cl.
CPC .................. *A61H 1/00* (2013.01); *A61N 5/00* (2013.01); *A61N 2005/0644* (2013.01)

(58) Field of Classification Search
None
See application file for complete search history.

(56) References Cited

U.S. PATENT DOCUMENTS 1,510,080 A   9/1924   Murphy
2,213,031 A   8/1940   Wolfskill
(Continued)

OTHER PUBLICATIONS

"Crystal Shapes Complete Correspondance Chart." Earth DNA, 2012. Web. Jul. 15, 2016.*
(Continued)

*Primary Examiner* — Gary Jackson
*Assistant Examiner* — Nathan A Baldwin
(74) *Attorney, Agent, or Firm* — Brian S. Steinberger; Law Offices of Brian S. Steinberger, P.A.

(57) ABSTRACT

Transducers, tools, devices, apparatus, systems and methods for rejuvenation and aging treatments. The invention can convert an input alternating current into a positive higher frequency output to energize a crystal pack or a plurality of crystals. The rejuvenation transducer includes an input power source to supply a lower frequency input current, a pulse generator to produce a positive higher frequency electrical output pulse from the lower frequency input current, a crystal pack coupled to receive the positive higher frequency electrical output pulse from the pulse generator and produce a gigahertz output and the crystal pack modulates the signal, and a light emitting diode in the current path to indicate an energized state of the rejuvenation transducer. Treatments with the transducers show telomere lengths being lengthened causing a rejuvenation effect.

10 Claims, 9 Drawing Sheets

Related U.S. Application Data

(60) Provisional application No. 61/924,368, filed on Jan. 7, 2014, provisional application No. 60/950,723, filed on Jul. 19, 2007, provisional application No. 60/685,448, filed on May 27, 2005.

(56) References Cited

U.S. PATENT DOCUMENTS

| | | | |
|---|---|---|---|
| 2,306,909 | A | 12/1942 | Sykes |
| 2,312,670 | A | 3/1943 | Olds |
| 3,371,234 | A | 2/1968 | Cady |
| 3,804,355 | A | 4/1974 | Uroshevich |
| 4,160,206 | A * | 7/1979 | Bojarski .............. G01R 15/12 324/133 |
| 4,221,986 | A | 9/1980 | Besson |
| 4,548,373 | A | 10/1985 | Komura |
| 4,708,127 | A | 11/1987 | Abdelghani |
| 4,739,507 | A | 4/1988 | Byer |
| 4,869,666 | A | 9/1989 | Talass |
| 4,930,504 | A * | 6/1990 | Diamantopoulos .. A61N 5/0616 250/494.1 |
| 5,086,788 | A | 2/1992 | Castel |
| 5,158,070 | A | 10/1992 | Dory |
| 5,230,334 | A | 7/1993 | Klopotek |
| 5,413,550 | A | 5/1995 | Castel |
| 5,464,436 | A | 11/1995 | Smith |
| 5,562,597 | A | 10/1996 | Van Dick |
| 5,591,219 | A | 1/1997 | Dungan |
| 5,824,007 | A | 10/1998 | Faraz |
| 5,989,202 | A | 11/1999 | Noda |
| 6,048,301 | A | 4/2000 | Sabuda |
| 6,113,559 | A | 9/2000 | Klopotek |
| 6,200,331 | B1 | 3/2001 | Swartz |
| 6,217,530 | B1 | 4/2001 | Martin |
| 6,238,421 | B1 | 5/2001 | Gunther |
| 6,500,198 | B1 * | 12/2002 | Southard ............. A61N 5/0616 607/2 |
| 6,520,903 | B1 * | 2/2003 | Yamashiro ........... A61N 5/0618 600/9 |
| 6,722,772 | B2 | 4/2004 | Maglica |
| 6,772,772 | B2 | 4/2004 | Maglica |
| 6,813,289 | B2 | 11/2004 | Gruzdev |
| 7,077,857 | B1 | 7/2006 | Crosby |
| 7,410,469 | B1 | 8/2008 | Talish |
| 7,410,769 | B2 | 8/2008 | Burroughs-Tencza |
| 7,883,534 | B1 * | 2/2011 | Crosby ................ A61N 5/0613 607/88 |
| 8,443,811 | B1 | 5/2013 | Crosby |
| 8,534,292 | B1 | 9/2013 | Crosby |
| 9,233,261 | B1 | 1/2016 | Crosby |
| 2003/0181949 | A1 * | 9/2003 | Whale ................. A61N 5/0613 607/2 |
| 2004/0002744 | A1 | 1/2004 | Dungan |
| 2004/0102810 | A1 * | 5/2004 | St. Clair ................. A61N 2/02 607/1 |
| 2004/0130896 | A1 | 7/2004 | Brown |
| 2005/0183739 | A1 | 8/2005 | McDermott |
| 2008/0060148 | A1 * | 3/2008 | Pinyayev ............. A61B 5/0088 15/22.1 |
| 2012/0265048 | A1 * | 10/2012 | Biggs ...................... A61B 5/05 600/409 |

OTHER PUBLICATIONS

Scherz, Paul, and Simon Monk. "3.8 Transformers." Practical Electronics for Inventors. McGraw-Hill Companies, 2013.*
Tseng, Kevin. "Protection Zener Series: A New Application in LED Field." Jul. 7, 2014.*
Solarraven, P. J. "Crystal Grids." Oct. 29, 2001.*
Mini Maglite Flashlight Specifications, 2003, http://web.archive.org/web/20030814145336/www.maglite.com/product_anatomy.asp?psc=2AACELL, 1 page.
Liss Body Stimulator, Professional Instrument Manual, SBL 502-B, 1994, pp. 1-8.
Crosby, Tenscam Professional Manual, 2001, pp. 1-8.
Oschman, J., Energy Medicine, The Scientific Basis, 2000, pp. 51, 61, 184.
Farzaneh-Far, R., et al., Telomere Length Trajectory and Its Determinants in Persons with Coronary Artery Disease: Longitudinal Findings from the Heart and Soul Study, Plos One, 2010, pp. 1-7, vol. 5, No. 1.
Kaszubowska, L., Telomere Shortening and Ageing of the Immune System, Journal of Physiology and Pharmacology, 2008, pp. 169-186, vol. 59, No. 9.
Fitzpatrick, A., et al., Leukocyte Telomere Length and Cardiovascular Disease in the Cardiovascular Health Study, American Journal of Epidemiology, 2006, pp. 14-21, vol. 165, No. 1.
Edo, M. et al., Aging, Telomeres, and Atherosclerosis, Cardiovascular Research, 2005, pp. 213-221, vol. 66.
Hund, Uses and Possibilities of Piezoelectric Oscillators, Proceedings of the Institute of Radio Engineers, 1926, pp. 447-469, vol. 14.
Raphaell, K., Lemurian Seed Crystals, Royal Priest Research, The Crystal Buzz International Newsletter, 1994, issue 12, 12 pages.

* cited by examiner

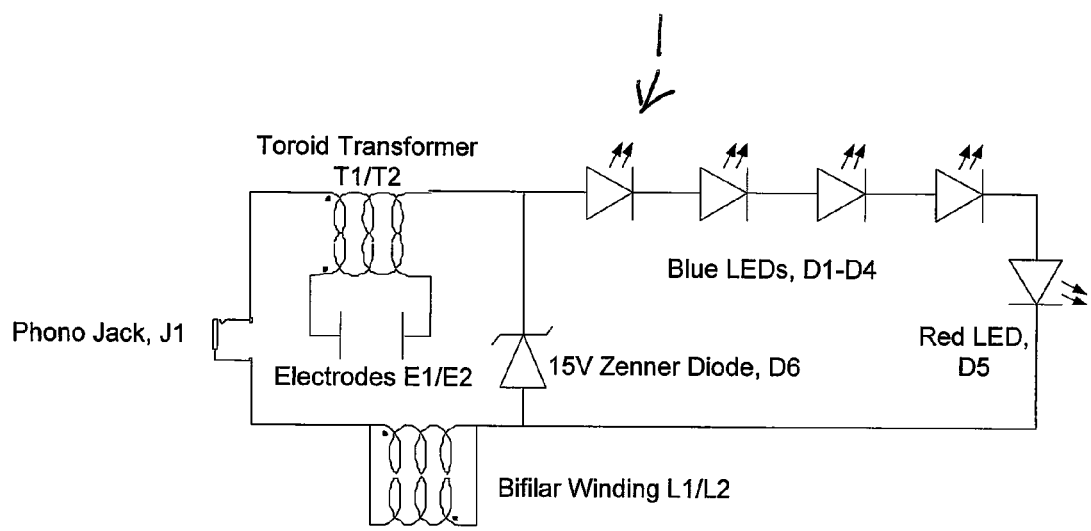
Fig. 1 Electrical Schematic for REJUVENATION TRANSDUCER

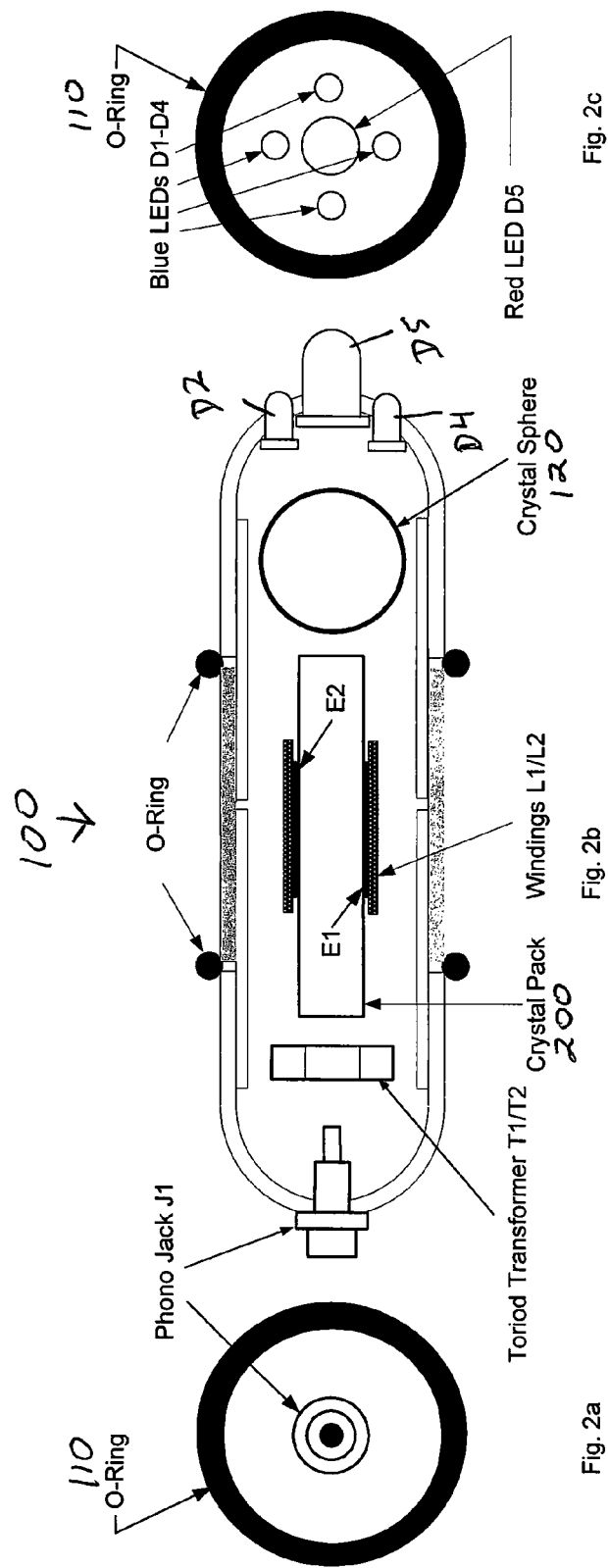

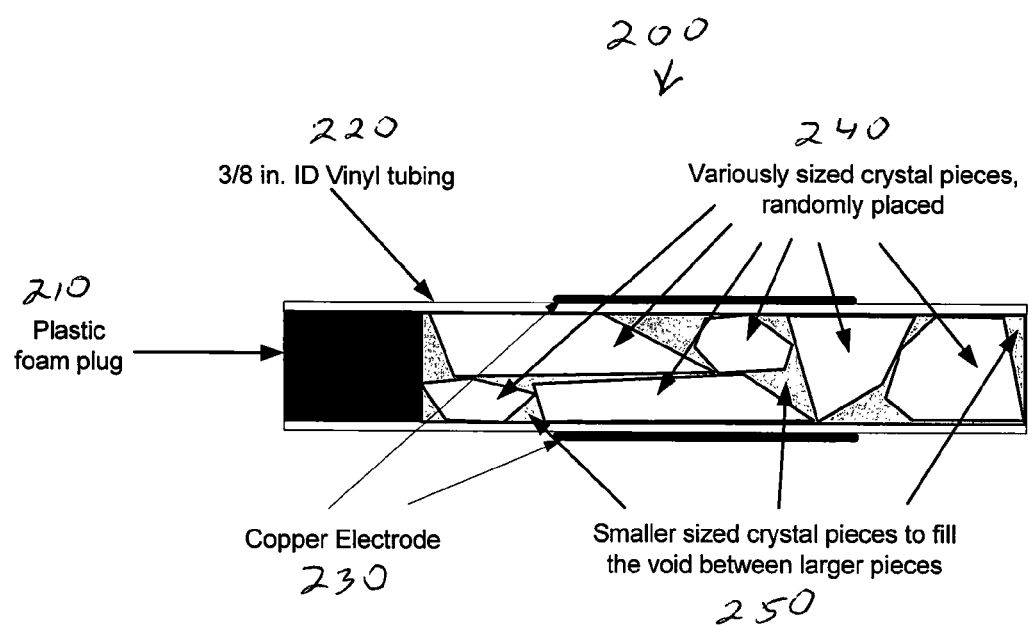
Fig. 3 Crystal Pack for the REJUVENATION TRANSDUCER

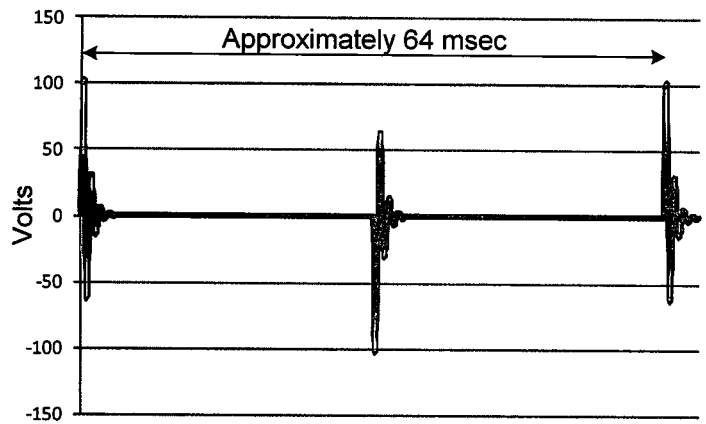
Fig. 4a Toroid Transformer Output Waveform
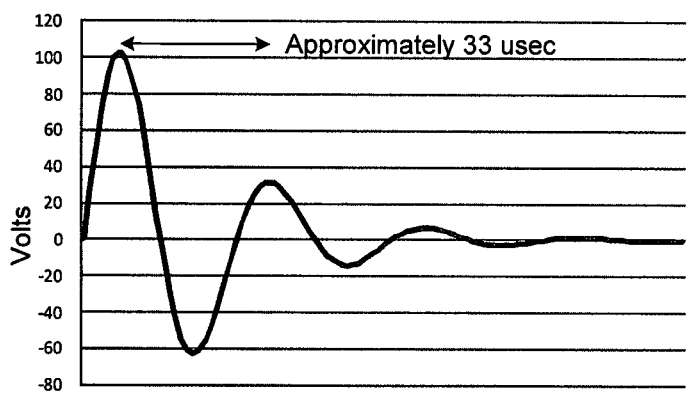
Fig. 4b Toroid Transformer Output Waveform at Input Pulse Turn On
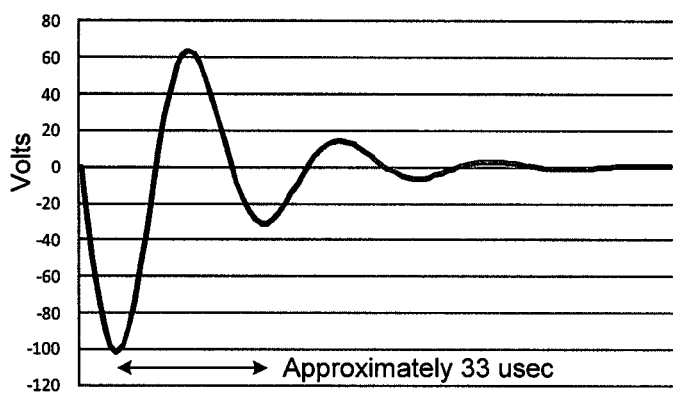
Fig. 4c Toroid Transformer Output Waveform at Input Pulse Turn Off

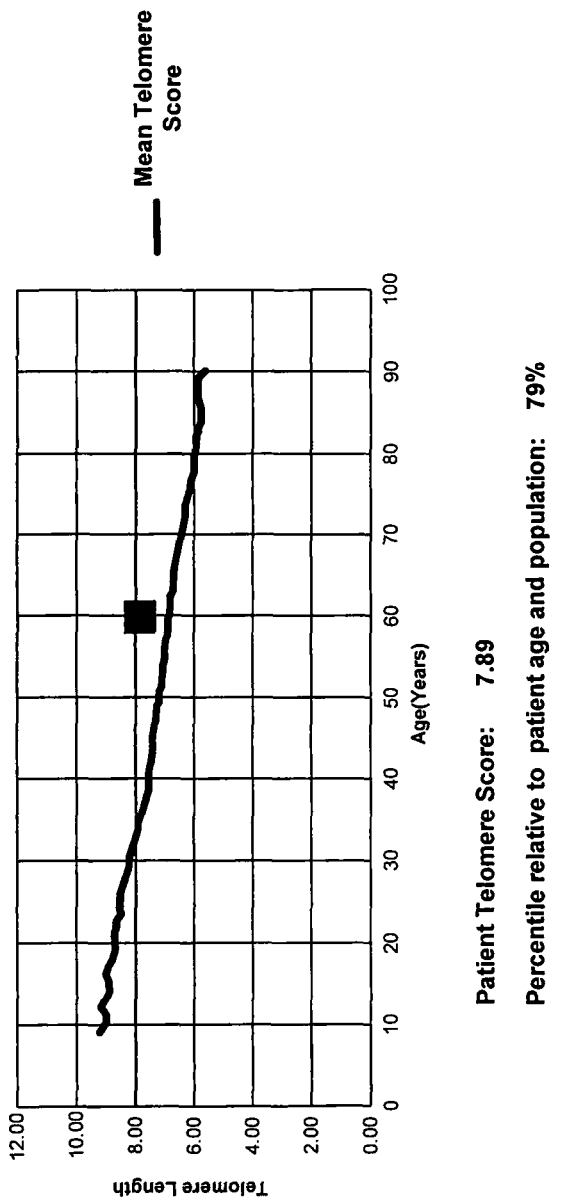

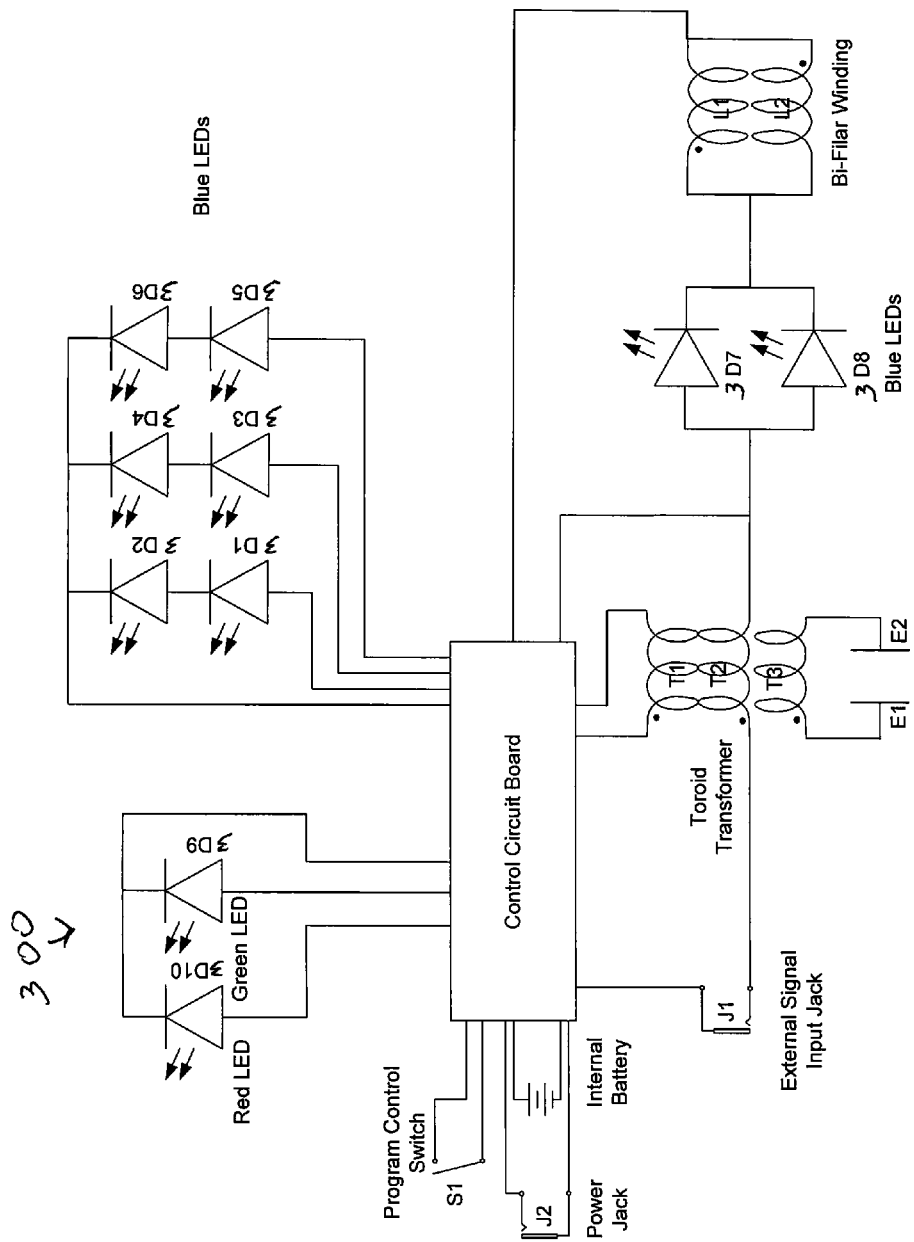
Fig. 6 Electrical Schematic for RJV-TensCam

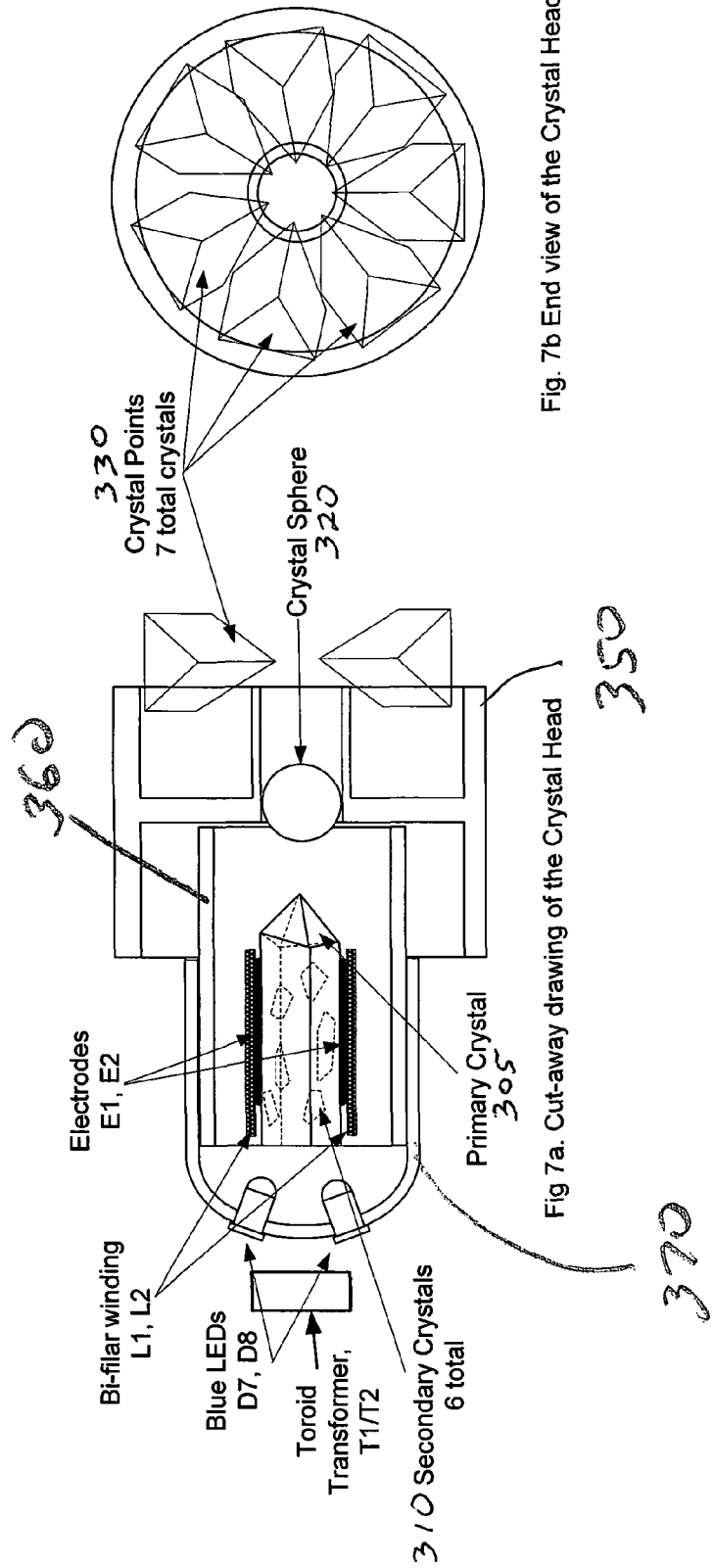

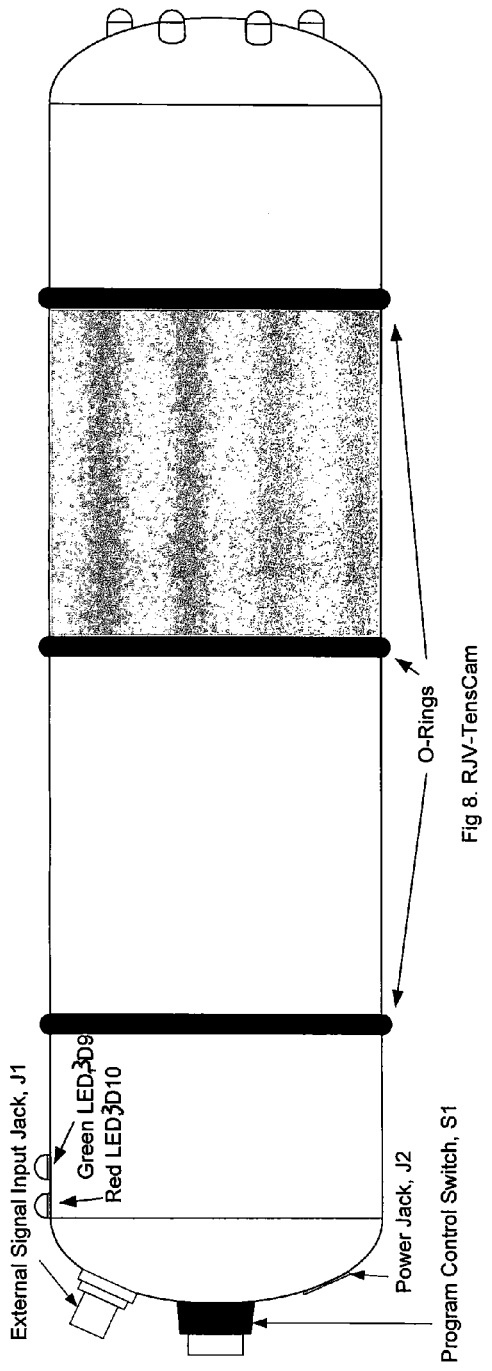
Fig 8. RJV-TensCam
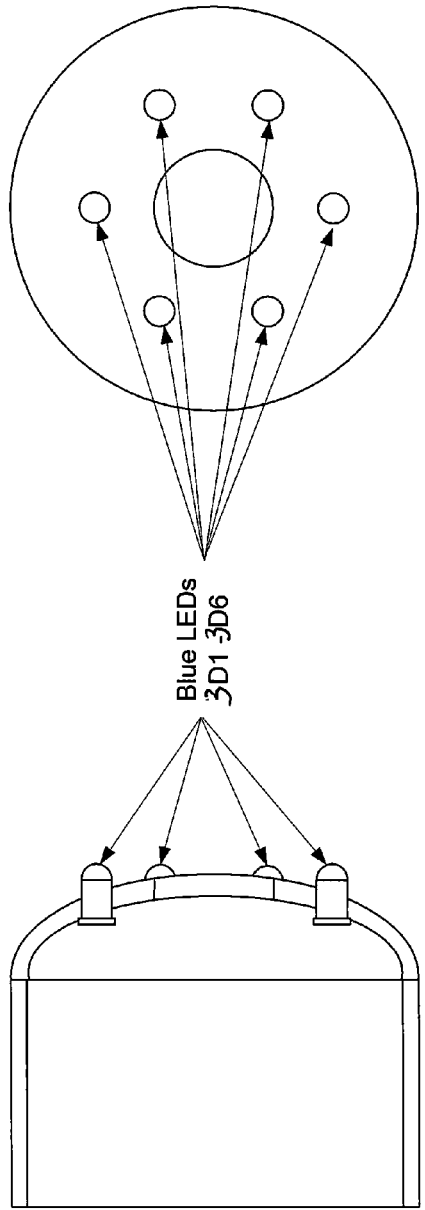
Fig 10. Front end view of the RJV-TensCam
Fig 9. Cut-away view of the front end cap

TRANSDUCER DEVICES, APPARATUS, SYSTEMS AND METHODS OF OPERATION

This application claims the benefit of priority to U.S. Provisional Patent Application Ser. No. 61/924,368 filed Jan. 7, 2014, and is a Continuation-In-Part of U.S. patent application Ser. No. 13/952,091 filed Jul. 26, 2013, now U.S. Pat. No. 9,463,332, which is a Continuation-In-Part of U.S. patent application Ser. No. 11/859,413 filed Sep. 21, 2007, now abandoned, which claims the benefit of priority to U.S. Provisional Patent Application Ser. No. 60/950,723 filed Jul. 19, 2007, and is a Continuation-In-Part of U.S. patent application Ser. No. 11/441,483 filed May 26, 2006, now U.S. Pat. No. 7,883,534, which claims the benefit of priority to U.S. Provisional Patent Application Ser. No. 60/685,448 filed May 27, 2005, and is a Continuation-In-Part of U.S. patent application Ser. No. 10/084,008 filed Feb. 27, 2002, now U.S. Pat. No. 7,077,857. The entire disclosure of each of the applications listed in this paragraph are incorporated by specific reference thereto.

FIELD OF INVENTION

This invention relates to medical transducers, and in particular to transducers, tools, devices, apparatus, systems and methods for therapy treatments with an energy generating source producing frequency pulses that does not have to be in contact with the skin surface of a patient and does not have the tissue depth penetration limitations of electromagnetic and vibratory devices, and can increase telomere lengths over time.

BACKGROUND AND PRIOR ART

One of the inventors, Dr. Charles Crosby was the inventor on U.S. Pat. No. 7,883,534 issued to Crosby on Feb. 8, 2011, which is incorporated by reference in its' entirety, describes a handheld flashlight type vibratory therapeutic treatment invention, devices, and methods that can house a small piezoelectric crystal adjacent to a bulb in the emitting chamber portion of a flashlight housing, where the crystal is located next to or between light source, or off-axis to the light emitting beam of the flashlight. The crystal can generate a fixed output of approximately 7 to approximately 8 Hertz while the flashlight body is positioned up to approximately 18 inches over the body part being treated with a light beam from the bulb being aimed at the area to be treated. Treatment effectiveness can occur within approximately 2 minutes of being treated. The flashlight invention can be used for treating a variety of ailments such as inflammations, nerve problems, joint pain, muscle pain, as well as gall bladder type problems.

U.S. Pat. No. 7,077,857 also issued to Crosby on Jul. 18, 2006, which is incorporated by reference in its' entirety, describes a battery powered and wall plug powered handheld therapy devices for treating a variety of ailments such as inflammations, nerve problems, joint pain, muscle pain, as well as gall bladder type problems. The device can have a multi-faced shaped emitting main crystal with side crystals that can be used with a flashing strobe light source to generate variable frequency pulses toward the effected body part to be treated. Alternatively, or additionally, the device can use an electromagnetic type generator to generate fixed frequency signals toward an effected body area to be treated. Up to approximately six small crystals or more can be positioned to a base portion of the emitting crystal on the six faces of the emitting crystal. The side crystals can be used as antennas to receive ambient energy in order to be focused by the main crystal. Hand grips or a floor based stand can be used to elevate the device up to approximately 18 inches above the patient. Effective treatment with the device has been achieved within approximately 2 minutes of use.

Thus, the need exists for solutions to the above problems with the prior art.

SUMMARY OF THE INVENTION

A primary objective of the present invention is to provide rejuvenation transducer tools, devices, apparatus, systems and methods for therapy treatments that does not have to be in contact with the skin surface of a patient; that does not have the tissue depth penetration limitations of electromagnetic sources and vibratory devices.

A secondary objective of the present invention is to provide rejuvenation transducers, tools, devices, apparatus, systems and methods for therapy treatments that can combine an energy generating source that produces higher frequency pulses for modulation/modification of aging process.

A third objective of the present invention is to provide rejuvenation transducers, tools, devices, apparatus, systems and method that can be used for treating aging effects.

A fourth objective of the invention is to provide transducers, tools, devices, apparatus, systems and methods for therapy treatments that can be handheld above a body part to be treated.

A fifth objective of the invention is to provide transducers, tools, devices, apparatus, systems and methods for therapy treatments that can increase telomere lengths of subjects being treated over time.

A preferred embodiment of a rejuvenation transducer can include a pulsed power source to supply a lower frequency input pulse, a pulse generator to produce a positive higher frequency electrical output pulse from the lower frequency input pulse, a crystal pack coupled to receive the positive higher frequency electrical output pulse from the pulse generator and modulate the signal to produce a therapeutic treatment, and a light emitting diode in the current path to indicate an energized state of the rejuvenation transducer.

The pulse generator can include an input connector to receive the lower frequency input pulse from a pulsed power source, a transformer having a primary and a secondary winding, the secondary winding producing a positive pulse, a light emitting diode, and a bi-filar winding consisting of inductor L1 and inductor L2 serially connected to the light emitting diode.

The transformer can include a toroid transformer with a primary to secondary winding ratio of approximately 1:10.

The pulse generator further can include a zener diode connected in parallel with the light emitting diode and the input power source to control current flow.

The crystal pack can include a tube containing a plurality of different sized quartz crystal pieces.

The rejuvenation transducer can include a handheld housing for supporting the pulsed power source, the pulse generator, the crystal pack, and the light emitting diode.

A method of rejuvenating a patient from a rejuvenation transducer, can include the steps of producing a lower frequency input pulse, generating a positive higher frequency electrical output pulse signal from the lower frequency input pulse, and modulating the output pulse signal to produce a therapeutic treatment from the rejuvenation transducer to increase telomere lengths.

The method of producing a low frequency input pulse, can include a low voltage power source, and a pulse generator.

The step of modulating the output pulse signal can include the step of providing a crystal pack coupled to receive the positive higher frequency electrical output pulse from the pulse generator.

The method can include the step of providing a light emitting diode to indicate an energized state of the rejuvenation transducer.

Another embodiment of the rejuvenation transducer can include a pulsed power source to supply a lower frequency input pulse, a pulse generator to produce a positive higher frequency electrical output pulse from the lower frequency input pulse, a plurality of crystals coupled to receive the positive higher frequency electrical output pulse from the pulse generator and modulate the signal to produce a therapeutic treatment, and a light emitting diode in the current path to indicate an energized state of the rejuvenation transducer.

The plurality of crystals can include a six sided elongated primary crystal with a pyramid tip, and electrodes attached to sides of the elongated crystal.

The rejuvenation transducer can further include a plurality of secondary crystals attached to other sides of the primary crystal.

The rejuvenation transducer can further include a spherical crystal mounted adjacent to the pyramid tip of the primary crystal.

The rejuvenation transducer can further include a plurality of crystal points in a circular arrangement mounted adjacent to the pyramid tip of the primary crystal.

The rejuvenation transducer can further include a Bi-filar winding wrapped about the electrodes and a toroid transformer connected to the electrodes.

Further objects and advantages of this invention will be apparent from the following detailed description of the presently preferred embodiments which are illustrated schematically in the accompanying drawings.

BRIEF DESCRIPTION OF THE FIGURES

FIG. 1 is an electrical schematic diagram showing a rejuvenation transducer embodiment according to the preferred embodiment of the invention.

FIG. 2a shows is an enlarged end view of the connector located at one end of the first embodiment rejuvenation (RJV) transducer housing.

FIG. 2b is a cut-away view of the first embodiment rejuvenation transducer housing showing the elements according to the preferred embodiment of the invention.

FIG. 2c is an enlarged end view of the red and blue LEDs located at an opposite end of the rejuvenation transducer housing.

FIG. 3 shows an example of a crystal pack for use with the rejuvenation transducer shown in FIG. 1.

FIG. 4a is a graphical representation of the output wave form from the toroid transformer.

FIG. 4b is a blow up of the transformer output when the input pulse turns on.

FIG. 4c is a blow up of the transformer output when the input pulse turns off.

FIG. 5 shows a telomere test results graph of telomere length verses age (years) for a test subject, with box showing the patient telomere score (PTS) relative to an elongated line showing the natural shortening of telomere length as a person ages.

FIG. 6 is an electrical schematic diagram showing a second embodiment RJV-transducer according to the preferred embodiment of the invention.

FIG. 7a is a cut-away drawing of the RJV-transducer crystal head for the second embodiment transducer FIG. 7b is an end view of the RJV-transducer crystal head for the second embodiment.

FIG. 8 is a representation of the second RJV-transducer.

FIG. 9 is a cut-away drawing of the front end cap of the second embodiment RJV-transducer.

FIG. 10 is an end view of the front of the second embodiment RJV-transducer.

DESCRIPTION OF THE PREFERRED EMBODIMENTS

Figure 11:
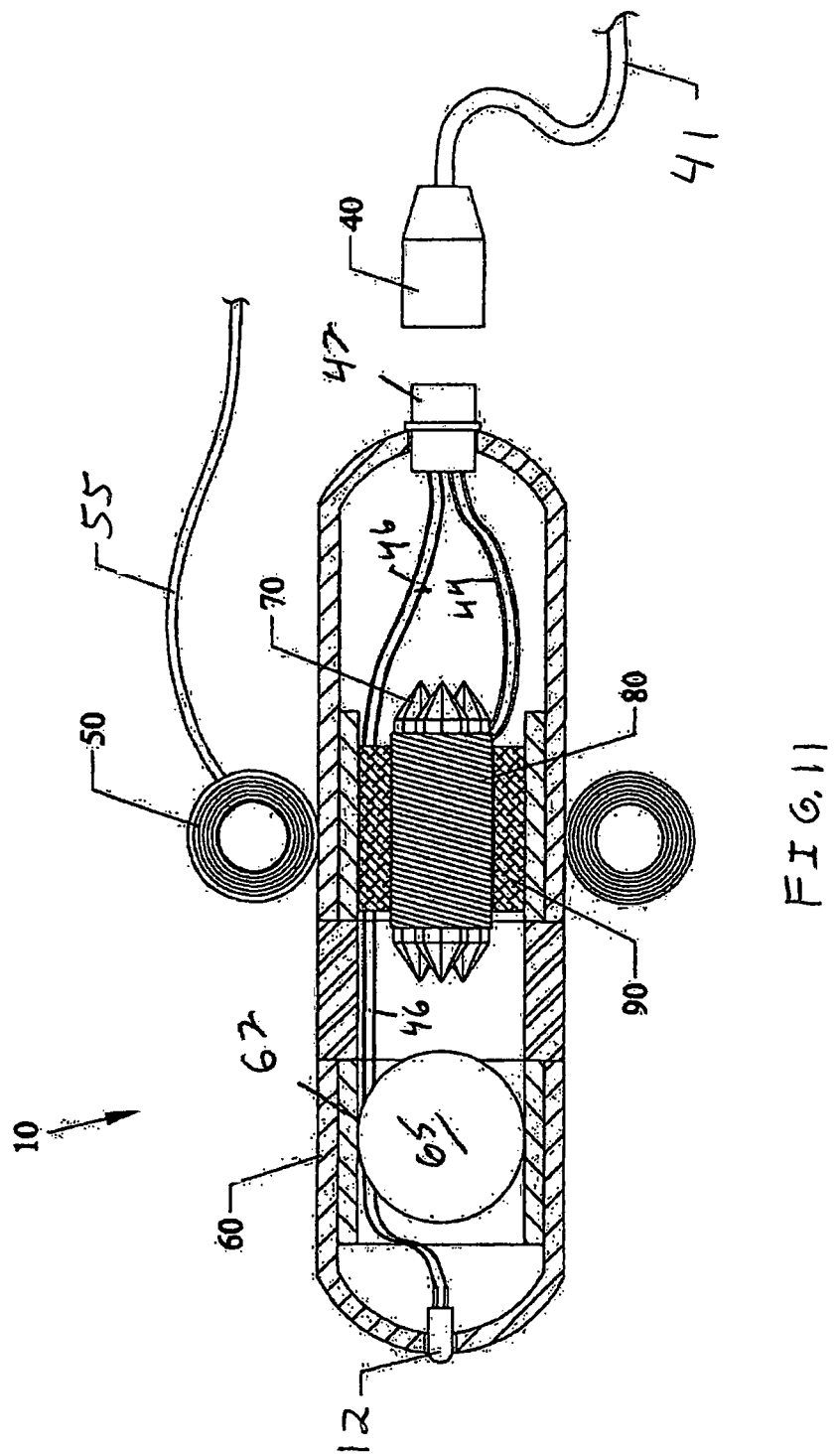
FIG. 11 is a cross-sectional view of an arrangement of the novel treatment device.

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

A description of each of the numbered components is now described.

10 Electrical Schematic
J1 Connector
T1 Toroid Transformer Primary Winding
T2 Toroid Transformer Secondary Winding
D1 Blue LED
D2 Blue LED
D3 Blue LED
D4 Blue LED
D5 Red LED
D6 zener diode
L1,L2 Bifilar conductor wound around the crystal pack
100 Transducer housing
110 O-ring(s)
120 quartz crystal sphere
200 Crystal pack
210 plastic foam plug
220 tubing
230 electrode
240 variously sized quartz crystal pieces randomly spaced
250 smaller sized quartz crystal pieces to fill void between larger crystal pieces.
300 electrical schematic diagram showing the RJV-Transducer
3D1 Blue LED
3D2 Blue LED
3D3 Blue LED
3D4 Blue LED
3D5 Blue LED
3D6 Blue LED
3D7 Blue LED
3D8 Blue LED
3D9 Green LED
3D10 Red LED
305 Primary Crystal
310 Secondary Crystals (6 total)
320 Crystal Sphere
330 Crystal Points (7 total)
350 modified plastic (such as PVC (polyvinyl chloride) adapter
360 pipe section (such as PVC section)
370 end cap (such as PVC end cap)

First Embodiment Rejuvenation (RJV) Transducer

FIG. 1 is the electrical schematic 1 for the rejuvenation transducer. Connector J1 can be an RCA panel mount phono jack (shown in FIG. 2a with O-Ring 110), that can be used to receive an input from a pulsed power source. Transformer (T1/T2) can be a toroid transformer with a primary (T1) to secondary (T2) winding ratio of approximately 1:10.

FIG. 2b is a cut-away view of the rejuvenation transducer 100 showing the positional relationship between the electrical components (J1, T1/T2, LEDS (light emitting diodes) (D1, D2, D3, D4, D5)) and the crystal pack 200 according to the preferred embodiment of the invention, and quartz crystal sphere 120 which can have a diameter from approximately ½' to approximately ¾" in diameter.

FIG. 3 shows an example of a crystal pack 200 for use with the rejuvenation transducer 100 according to the present invention. FIGS. 2a and 2c show the ends of the rejuvenation transducer housing with O-ring(s) 110 to show the location of the input connector J1, at one end and the light emitting diodes D1, D2, D3, D4 and D5, at the opposite end.

As shown in FIG. 2b the electrodes 230, E1 and E2, are placed on opposite sides of the crystal pack 200.

In a preferred embodiment, light emitting diode D5 can be a 10 mm diameter red LED mounted in the center of the end cover which is used as an activity indicator. The four light emitting diodes D1, D2, D3, and D4 surrounding the red D5 can each be a 5 mm diameter, 470 nm blue LEDs with 15 degree lenses that produce an average illumination of approximately 11,000 milli-candles each. The light from LEDs D1-D4 can be used for treating drug resistant bacterial infections.

Diode D6, which is shown in parallel with the LEDs, can be a 1 watt, 15 Volt, zener diode which is used to provide a circuit path through the transducer when a negative voltage pulse is applied to the input connection J1. The zener diode D6 also provides over-voltage protection for the LEDs, D1-D5.

Referring to the circuit 1 of FIG. 1 in conjunction with FIG. 2b, the current path continues through L1 and L2, which can be bifilar windings around a quartz crystal pack. L1 and L2 each can have approximately 375 turns wound around the crystal pack 200.

Referring to FIG. 3, the crystal pack 200 can include a ⅜" inside diameter (ID) vinyl tube that is closed at one end and has a plastic foam plug 210 to seal the other end of the vinyl tube 220. Enclosed within the vinyl tube 220 can be a variety of different sized quartz crystal pieces 240. The larger quartz crystal pieces 240 can randomly fill the vinyl tubing 220 with smaller crystal pieces 250 filling in the spaces between the larger crystal pieces 240. The sizes of the crystal pieces range between one that will just fit into the vinyl tube. The large crystal pieces 240 can be odd shapes, such as any broken up quartz pieces having a range of less than approximately ⅜" down to approximately ⅛". The smaller quartz crystal pieces 250 can be the size of grains of sand (in millimeters up to less than approximately 1/16).

As shown in FIG. 3, the inductors L1 and L2 can be positioned along the length of the vinyl tube 220 to further energize the quartz crystals 240, 250 at a frequency set by the driving waveform, approximately 16 Hz.

As shown in FIG. 2, the rejuvenation transducer can include a quartz crystal sphere 120 approximately three quarters of an inch in diameter to defocus the energy output. The crystal pack 200 containing an array of crystals 240, 250 can be coupled to receive the approximately 16 Hz pulses from inductors L1 and L2.

Those skilled in the art will understand that the materials and sizes are to illustrate the preferred embodiment, although different configurations can be substituted.

Functional Description of the Rejuvenation (RJV) Transducer

Referring to FIGS. 1-3, an external driver supplies, through J1, a pulsed voltage which can be approximately 3.3 to approximately 5 volts peak to peak. The current resulting from that voltage passes through the primary winding of the toroid transformer, T1, which causes the secondary winding, T2, to apply a higher voltage between electrodes E1 and E2.

The resulting voltage wave form is depicted in FIGS. 4a, 4b and 4c, and is a differentiated form of the pulse supplied to the primary winding, T1. When the input voltage switches from low to high, it generates a damped waveform that begins with a positive going oscillation as depicted in FIG. 4b. When the input voltage switches from high to low, it generates a damped waveform that begins with a negative going oscillation as depicted in FIG. 4c.

FIG. 4a shows the composite output signal for one cycle of the input current. The effect of the signal placed between E1 and E2 is to excite the crystal pack with energy derived from the sharp voltage spikes, both positive and negative, each of which contains high frequency components, which in turn cause the field generated by the crystals to be modulated at a high frequency that can be between 54 GHz and 84 GHz.

Referring to FIGS. 1-3, the current continues through LEDs D1-D5, illuminating them during the positive half-cycle of the input voltage, and through zener diode D6 during the negative half-cycle of the input voltage. D6 limits the voltage applied across diodes D1-D5 to 15 volts to protect them from damage during the positive half-cycle; it also provides a current path around diodes D1-D5 during the negative half-cycle.

The current continues through the windings L1 and L2. The windings are configured in a bifilar manner and the current is passed through both windings simultaneously in opposite directions, which causes a minimal magnetic field to be generated by the winding while maximizing the opportunities for electron near misses. When a near miss between two electrons occurs, a virtual photon (as described in "A Brief History of Time, Stephen W. Hawking, 1988, page 69) can be generated which has all the attributes of a photon, except being visible. The effect of the virtual photons on the crystals 240 is to excite the crystals 240 in the crystal pack 200 and to cause a modulation of the field generated by the crystals at a frequency determined by the input voltage, approximately 16 Hz.

Effective treatment with the device has been achieved within fifteen minutes of use twice daily.

Second Embodiment RJV-Transducer

Another preferred embodiment of the rejuvenation transducer can include a multi-mode design that allows the separation of the high and low frequency effects and can be used in a manner similar to the rejuvenation transducer.

FIG. 6 is the electrical schematic 300 for the second embodiment RJV-Transducer. The Control Circuit Board contains an approximately 3.3 volt voltage regulator, a microprocessor, a battery charging circuit, and appropriate switching transistors. The voltage regulator can be supplied power from a 3.7 volt NiMH battery. J1 is a panel mount RCA phono jack which can be used to receive an external drive input. J2 can be a panel mount 2.1 mm power connector through which the power is supplied by an external power source to the on board charging circuit.

The charging circuit can be used to charge the internal battery. S1 can be a momentary, normally open panel mount switch that is used to select the various modes of the RJV-Transducer. Diodes 3D1, 3D2, 3D3, 3D4, 3D5 and 3D6 can each be 470 nm blue LEDs which are mounted in the front end cap as illustrated in FIGS. 8, 9 and 10.

The blue LEDs, 3D1-3D6, can be switched on and off appropriately by on board transistors controlled by the microprocessor. FIG. 7a is a cut-away drawing of the internal crystal head which shows the relative positioning of the primary quartz crystal 305, electrodes E1 and E2, bifilar windings L1 and L2, LEDs 3D7 and 3, the quartz crystal sphere 320, and an array of seven quartz crystal pieces 330 called points.

FIG. 7b is an end view drawing of the crystal head showing the relative positions of the seven crystal points 330. Diodes 3D7 and 3D8 are also 470 nm blue LEDs which are mounted internally such that their light output is focused at the end of the primary quartz crystal 305. The structure of the crystal head can be machined PVC plastic, as is the outer housing RJV-Transducer.

FIG. 8 is an external view of the RJV-Transducer which shows the positions of LEDs 3D1-3D6 of the front end cap, LEDs 3D9 and 3D10, connectors J1 and J2, and Program Control Switch S1 on the back end cap 370.

FIG. 9 is a cut-away drawing of the front end cap showing the placement of LEDs 3D1-3D6. FIG. 10 further defines the positions of LEDs 3D1-3D6. Diode 3D9 is a green LED and diode 3D10 is a red LED and are mounted on the back end cap to indicate the selected mode. T1/T2 is a toroid transformer which is used in the higher frequency, or rejuvenation, mode. It is typically mounted to the back end of the crystal head.

Description of the Second Embodiment
RJV-Transducer

External Drive Mode

Referring to FIGS. 6-10, the RJV-Transducer can be driven by an external source such as is used with the rejuvenation transducer by connecting the output of the external source to the RCA phono connector, J1, located on the back end cap of the RJV-TensCam housing. The equivalent circuit in that mode is identical to the rejuvenation transducer circuit 1, except that the primary crystal 305, augmented by six (6) additional crystal chips 310, replaces the crystal pack 200 and is further excited by addition of pulsed 740 nm light from the blue LEDs, 3D7 and 3D8.

Primary crystal 305 can be a natural grown quartz crystal typically having six flat sides with a narrow pyramid shaped point, having a thickness of approximately ¼" up to approximately ½", and a length of approximately 1.5" to approximately 2.5".

The electrodes E1, E2 are adhered on opposite sides of the six sided primary crystal 305.

Secondary crystals 301 can each be small broken quartz crystal pieces (similar to the smaller pieces described in the previous embodiment), and these secondary crystals 301 can be adhered (for example, by glue, and the like) along the other sides of the primary crystal 305 where the electrodes E1, E2 are not located. The Bi-filar winding L1, L2 is then wrapped around both the electrodes, E1, E2 and the adhered secondary crystals 310.

Crystal sphere 320 can be a spherical quartz crystal similar the one described in the previous embodiment and can have a diameter from approximately ½' to approximately ¾" in diameter.

Crystal points 330 can be 7 naturally grown quartz crystals each having a pyramid shape arranged in a circle turned so that each of the apex tips are pointed toward the middle of the circle. Each of the 7 crystals 330 can have a base of approximately ⅜" to approximately ⅝", and a length of approximately ½". The 7 crystal points 330 can be adhered to a modified adapter 350, which can be a 2" to ½"(or 2" to ¾") PVC type pipe adapter, which has been cut down. The crystal sphere 320 can be adhered into the smaller diameter of the adapter 350, and the crystal points 330 adhered to a front end of the cut adapter 350. An approximately 1' cut PVC type pipe section 360 is adhered to the opposite side, with an approximately 1" PVC type end cap 370 adhered to the outside of the pipe section 360. The adhering can include but is not limited to glue, and the like.

In this mode, the T1 winding of the toroid transformer is unused and the input current in passed through the T2 winding, causing the secondary winding, T3, to produce a higher voltage waveform similar to what is shown in FIGS. 4a, 4b and 4c. The windings completely cover the electrodes E1 and E2 and tend to reflect the electric field generated by the electrodes in the high frequency mode back into the crystal 305, thus maximizing the high frequency effect and minimizing the overall electric field.

The actual voltage waveform of the output will be dependent on the signal supplied by the external source. The input current through T2 flows through the blue LEDs, 3D7 and 3D8, which are mounted such that they will pulse the blue light energy into the primary crystal 305 as illustrated in FIG. 7a.

The light energy can be used to excite the crystals 305, 310, 320, 330, referenced above to cause the low frequency effect. The crystals 305, 310, 320, 330 are further excited by passing the current through the blue LEDs, D7 and D8 into the bifilar winding L1, L2 around the primary crystal 305. The bifilar windings are constructed such that nearly identical currents pass through the two windings in opposite directions. That arrangement minimizes the magnetic field which is generated by the winding while maximizing the opportunities for electron near misses. When two electrons come close to colliding, a virtual photon (such as those described in A Brief History of Time, Stephen W. Hawkings, 1988, p 69) generated which has all the attributes of a photon, except being visible.

The effect of the virtual photons is to augment the actual photons being focused on the primary crystal 305 and increase the low frequency effect. The quartz crystal sphere 320 as depicted in FIG. 7a acts as a diffuser of the output of the primary crystal 305. The output of the sphere 320 is directed through the array of 7 quartz crystal points 330 arranged around the path of the energy which has the effect of increasing the output of the total system.

Internal Control Mode

Referring to FIGS. 6-10, the RJV-Transducer can also be operated by a battery powered, microprocessor controlled, driver circuit board (control board) which is internal to the RJV-Transducer. Such components have been described in the inventor and assignees previous patents. See for example, U.S. Pat. No. 8,534,292 to Crosby; U.S. Pat. No. 8,443,811 to Crosby; U.S. Pat. No. 7,883,534 to Crosby; and U.S. Pat. No. 7,077,857 to Crosby, which are all incorporated by reference in their entirety.

A momentary, normally open, switch (S1) is mounted on the back end cap of the RJV-Transducer housing. The operating mode of the device can be selected by pushing the switch button a specific number of times. It is not intended that the device would be operated in both the external mode and the internal mode at the same time.

Flashlight Mode

Assuming that the device is off to begin with, the first time the switch, S1, is pushed, the six 740 nm blue LEDs, 3D1-3D6, are turned on and no other internal effects are activated. In this mode the control circuit board will turn off after two minutes.

Low Frequency Mode

Referring to FIGS. 6-10, when the switch, S1, is pushed a second time, the blue LEDs, 3D1-3D6, will begin to flash at approximately 16 Hz and the low frequency effects generator will function, pulsing in sync with the flashing LEDs. In that mode, green LED, 3D9, will also flash in sync with the diodes 3D1-3D6 as a mode indicator. The microprocessor controlled circuit board supplies a stream of voltage pulses that switch between 0 and 3.3 volts directly to the blue LEDs, 3D7 and 3D8. The pulse on-time and the pulse off-time are individually randomly modulated by as much as 50% of their average value.

The average pulse rate can be approximately 15.66 Hz and the average duty cycle is approximately 50%. The pulsed voltage drives blue LEDs, 3D7 and 3D8, and the bifilar winding and causes the crystals to respond in the same manner as is described in the external input section above. In this mode the control circuit board will turn off after two minutes.

High Frequency Mode

When the switch, S1, is pushed a third time, LEDs 3D1-3D6, will continue to flash at approximately 16 Hz, the low frequency function stops, and the high frequency effects generator will function, pulsing in sync with the flashing LEDs. In this mode, the green indicator LED, 3D9, turns off, and the red indicator LED, 3D10, will flash in sync with the blue LEDs 3D1-3D6. The high frequency effect is produced by driving a pulsed current through transformer winding, T1. The toroid transformer, T1/T2/T3, has a turns ratio of 1:1:10 respectively, which is identical in function to the transformer used in the rejuvenation transducer.

The output voltage waveform is applied to electrodes E1 and E2. In this mode the LEDs 3D7 and 3D8 and the bifilar windings are not used. The total input of energy to the crystals is done through applying the output of the toroid transformer to electrodes E1 and E2. This causes a voltage waveform at the electrodes similar to the one shown in FIGS. 4a-4c. The output field is thus modulated by the higher frequency energy, which can be between approximately 54 GHz and approximately 84 GHz. In this mode the control circuit board will turn off after fifteen minutes.

Shut Down

When the switch, S1, is pushed a fourth time, everything turns off.

Application of the RJV-Transducer

The low frequency mode works in approximately 2 minutes, once daily, and has been tested and shown to relieve pain and inflammation; kills bacteria. The higher frequency mode, can be used for rejuvenation, can work in approximately 15 minutes, twice daily. The RJV-Transducer can apply approximately 54 GHz to approximately 84 GHz frequencies which have been shown to lengthen telomeres.

The RJV-Transducer combines several elements to balance and harmonize the human energy field—thus reducing pain, inflammation, and bacterial infection. It is also being used to provide specific frequencies in the gigahertz (GHz) range which have been associated with natural lengthening of telomeres. "Telomeres are responsible not only for the length of life but also the integrity of DNA . . . . Rejuvenation or re-growth of telomeres is, therefore, a major key to longevity and health.", Norman Shealy, MD PhD.

The resonant frequency of the Earth is 7.83 Hertz (Hz). This frequency (the Schumann resonance) has been called the tuning fork for life; it has a balancing effect on all life forms. When applied appropriately, the Schumann resonance balances and coheres the human energy field, often resolving a variety of symptoms. Earth's most abundant mineral (quartz) has played a pivotal role in ushering in our techno-logical age. Quartz crystals are widely used in solid state technology. In the RJV-TensCam, they change light/electrical input to scalar output.

Scalar energy is a very fine form of energy that makes up the human energy field. According to Dr. Valerie Hunt, a former neurophysicist at UCLA (University of California, Los Angeles), scalar energy activates the human bio-scalar energy field and supports the healing response.

The above elements can be used in the rejuvenation transducer along with conscious intention to bring relief of many symptoms—without chemical or mechanical intervention.

How does the Transducer Work?

Since the 1950s, scientists have known that the human body naturally resonates at approximately 7.83 Hz. Areas of the body exhibiting pain and/or inflammation (or imbalance in other ways), no longer vibrate at this frequency. The RJV-TensCam helps re-establish the body's normal frequency and balance the bio-energetic field. This is critical for the resolution of pain and for the return to health.

How do I Use the Transducer

Simply turn on and point the unit at the problem area from a distance of approximately 18 inches (½ meter) for the green LED 2 minutes, once daily, with the intent to heal.

Progress can be monitored in real-time with manual energy evaluation, muscle testing, or a standard ultrasound scanner. Edema can be seen to re-solve first, followed by restructuring of tissue planes. Visual observation reveals an almost immediate decrease in swelling and redness associated with inflammation. Thermography confirms changes in skin temperature. Relief of pain is often immediate.

Different types of mode operations without the subject invention telomere therapy have been described in U.S. Pat. No. 8,534,292 to Crosby; U.S. Pat. No. 8,443,811 to Crosby; U.S. Pat. No. 7,883,534 to Crosby; and U.S. Pat. No. 7,077,857 to Crosby, which are all incorporated by reference in their entirety.

FIG. 11 is a cross-sectional view of an arrangement of the treatment device in a housing 60 having a tip with an indicator LED (light emitting diode) 12 in front of a crystal sphere 65 inside of a pressure fit, with conductors 44, 46, and a male connector 42 which is mateable to a female connector 40 that connects to a cable 41, the components of which can function similar to the embodiment in FIG. 2A.

Inside a mid-part of the housing 60 can be three (3) elongated multi-faceted crystals 70, such as lemurian crystals, preferably arranged in a triangular configuration. Each of the elongated crystals can have dimensions of approximately 1 inch long and approximately ¼ inch in diameter. Although three (3) crystals are shown and described, it is possible for the invention to work with more crystals, such as four or more. The triangular arrangement of crystals 70 can be wrapped in a bifilar coil 80, which functions as an inner coil to cancel out the magnetic component. The inner coil can include up to approximately 400 winding turns. The wrapped crystals 70 within the inner coil 80 can be supported within the housing 60 by an insulative cushion sleeve 90 such as wrapped electrical tape, foam, combinations thereof, and the like.

Surrounding the housing 60 can be an external coil 50, such as a torroidal coil, connected to an amplifier using connecting cable 55 which is used to pick up the sensed variance from the three crystals 70, which can function similar to the previously described embodiment.

Transducer Blue Light Treatment

Inflammation and pain are often associated with microbial infection. Recent research has demonstrated that blue light at a wavelength of approximately 470 nanometers (nm) effectively controls many types of bacteria including periodontal bacteria, acne, and resistant types of *staphylococcus* (MRSA). The 470 nm wavelength of visible light has been shown effective for both gram positive and gram negative bacterial strains.

The RJV-Transducer can include blue lights at the 470 nm wavelength. When the RJV-Transducer is held approximately 1 cm (3/8 inch) from the skin, many types of bacteria and other microbes can be significantly reduced. Treatment for 2 minutes every approximately 4 to approximately 6 hours for approximately 3 or approximately 4 days can often replace antibiotics and their side effects.

Telomere Testing after Treatments with the Invention

Test studies were conducted with the invention being used to treat multiple adult subjects. Telomere testing of the subject's blood by Spectracell Laboratories, of Houston, Tex., and Diagnostic of British, Columbia in 2013 and 2014. Telomeres are special functional complexes, and are protective tips located at the ends of chromosomes, that are involved in maintaining genetic stability and in regulation of cellular life span. Telomeres are sections of genetic material at the end of each chromosome whose primary function is to prevent chromosomal "fraying" when a cell replicates. As a cell ages, its telomeres become naturally shorter. Eventually, the telomeres become too short to allow cell replication, the cell stops dividing and will ultimately die, which is part of the normal biological process. A telomere test can determine the length of a patient's telomeres in relation to the patient's age.

Telomere homeostasis is relevant to normal aging and a wide range of disease states, including cancers, cardiovascular diseases and age-related disorders. As somatic cells proliferate, telomeres progressively shorten and the measurements of telomere length has emerged as an important determinate of replicative senescence and cell fan-an important indicator of the aging process. Telomere testing is used to accurately measure the human biological age, and if done at different times can show aging of the subject. Serial evaluation of telomere length on different dates can be an indicator of how rapidly one ages relative to a normal population.

Telomere length can be affected by age, paternal age at birth, gender, elevated levels of oxidative stress and inflammation, menopausal status, and low levels of physical activity. Increases in telomere loss may point to an increase in immunoproliferation, inability to handle oxidative stresses or progression of chronic disease and metabolic abnormalities.

FIG. 5 shows a telomere test results graph of telomere length verses age (years) for a test subject, with box showing the patient telomere score (PTS) relative to an elongated line showing the natural shortening of telomere length as a person ages. The telomere length is determined using a ratio of the genetic material contained in a nucleated white blood cell telomere relative to the length of a single copy gene of known size to calculate an approximate telomere score. This ratio is compared to a population of people with similar chronological age.

For each of the test subjects treated by the invention, blood tests were taken twice, each after a treatment occurred using the invention above. Generally, The blood tests were analyzed and provided a telomere length at the end of chromosomes, where the higher the telomere length, the younger the person is relative to their age. Table 1 shows patent telomere score (PTS) and percentage (%) to patient age values for five subject patients that were provided treatments with the novel invention with the testing done by Spectracell Laboratories.

TABLE 1

| SUBJECT Date of Birth (DOB) | TREATMENT DATES FIRST DATE SECOND DATE | PTS (PATIENT TELOMERE SCORE) | % TO PATIENT AGE |
|---|---|---|---|
| CK(female) Feb. 20, 1955 | Feb. 20, 2013 Mar. 26, 2014 | 8.61 9.13 | 90% 96% |
| CK(male) Jul. 11, 1935 | Feb. 20, 2013 Mar.11, 2014 | 6.23 5.64 | 51% 38% |
| BN(female) Dec. 28, 1956 | Mar. 5, 2013 Dec. 31, 2013 | 5.93 6.6 | 18% 37% |

Table 2 shows patent telomere score (PTS) and percentage (%) to patient age values for a single subject that was provided treatments with the novel invention with both testings done by Repeat Diagnostics of North Vancouver, British Columbia.

TABLE 2

| SUBJECT Age Age | TREATMENT DATES FIRST DATE SECOND DATE | PTS AVERAGE (PATIENT TELOMERE SCORE) | % TO PATIENT AGE |
|---|---|---|---|
| NB(female) | | | |
| Age 62 Age 63 | Feb. 21, 2013 Aug. 29, 2013 | 5.05 6.05 | 5% 30% |

Table 3 shows patent telomere score (PTS) and percentage (%) to patient age values for several test subject that were provided treatments with the novel invention and with a first testing done by Repeat Diagnostics of North Vancouver, British Columbia, and the second testing done by Spectral Laboratories.

TABLE 3

| SUBJECT Date of Birth (DOB) | TREATMENT DATES FIRST DATE SECOND DATE | PTS (PATIENT TELOMERE SCORE) | % TO PATIENT AGE |
|---|---|---|---|
| GH(female) May 31, 1948 | Jan. 24, 2013 Jan. 8, 2014 | 6.6 6.48 | 35% 44% |
| RK(male) Jun. 26, 1944 | Jan. 24, 2013 Aug. 20, 2013 | 7.1 7.49 | 65% 79% |
| WK(female) May 23, 1950 | Jan. 24, 2013 Aug. 20, 2013 | 9.2 8.36 | 90% 90% |

Tables 1, 2 and 3 provide evidence that increasing the telomere lengths in subjects that have been treated with the invention, wherein the increase in telomere length causes a rejuvenation effect in the subjects being treated.

The term "approximately" used above can include +/- value amounts of the listed number value. Additionally, the numbered values can include exact numbered values listed without the term "approximately."

The telomere testing of the invention test subjects shows that telomere length is shown be positively affected by treatments of the subjects when using the novel invention. Other applications of the invention can be used for reducing swelling in ones' eyes within approximately 20 minutes.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A rejuvenation transducer comprising:
   a pulsed power source to supply a first frequency electrical input pulse;
   a pulse generator to produce a positive second frequency electrical output pulse from the first frequency electrical input pulse, the second frequency electrical output pulse being a greater frequency than the first frequency electrical input pulse;
   a crystal pack coupled to receive the positive higher frequency electrical output pulse from the pulse generator and modulate the signal to produce a therapeutic treatment, the crystal pack comprising a plurality of at least three crystals wherein the plurality of at least three crystals includes a triangular arrangement; and
   an activity indicator light emitting diode in a current path with the pulse generator to indicate an energized state of the rejuvenation transducer, wherein the pulse generator comprises:
   an input connector to receive the lower frequency input pulse from a pulsed power source; and
   a bi-filar winding wrapped about all of the plurality of the crystals in the crystal pack, the bi-filar winding consisting of inductor L1 and inductor L2 serially connected to the activity indicator light emitting diode.

2. The rejuvenation transducer of claim 1 wherein the pulse generator further comprises:
   a zener diode connected in parallel with the activity indicator light emitting diode and the input power source to control current flow.

3. The rejuvenation transducer of claim 1 wherein the crystal pack comprises:
   a tube containing a plurality of different sized quartz crystal pieces.

4. The rejuvenation transducer of claim 1, further comprising:
   a handheld housing for supporting the pulsed power source, the pulse generator, the crystal pack, and the activity indicator light emitting diode.

5. A rejuvenation transducer comprising:
   a pulsed power source to supply a first frequency input pulse;
   a pulse generator to produce a positive second frequency electrical output pulse from the first frequency input pulse, the second frequency electrical output pulse being a larger frequency than the first frequency input pulse;
   a plurality of crystals coupled to receive the positive higher frequency electrical output pulse from the pulse generator and modulate the signal to produce a therapeutic treatment, wherein the plurality of at least three crystals includes a triangular arrangement;
   a six sided elongated primary crystal with a pyramid tip;
   a bi-filar winding wrapped about all of the plurality of crystals: and
   an activity indicator light emitting diode in a current path with the pulse generator to indicate an energized state of the rejuvenation transducer.

6. The rejuvenation transducer of claim 5, further comprising:
   a plurality of secondary crystals attached to other sides of the primary crystal.

7. The rejuvenation transducer of claim 6, further comprising:
   a spherical crystal mounted adjacent to the pyramid tip of the primary crystal.

8. The rejuvenation transducer of claim 6, further comprising:
   a plurality of crystal points in a circular arrangement mounted adjacent to the pyramid tip of the primary crystal.

9. The rejuvenation transducer of claim 5, further comprising:
   a spherical crystal mounted adjacent to the pyramid tip of the primary crystal.

10. The rejuvenation transducer of claim 9, further comprising:
    a plurality of crystal points in a circular arrangement mounted adjacent to the pyramid tip of the primary crystal.

* * * * *